United States Patent [19]

Kinast et al.

[11] Patent Number: 4,489,076
[45] Date of Patent: Dec. 18, 1984

[54] CEPHALOSPORINS

[75] Inventors: Günther Kinast; Michael Boberg; Karl G. Metzger, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 542,833

[22] Filed: Oct. 17, 1983

[30] Foreign Application Priority Data

Oct. 23, 1982 [DE] Fed. Rep. of Germany ....... 3239365

[51] Int. Cl.³ ................ C07D 501/38; A61K 31/545
[52] U.S. Cl. ..................................... 424/246; 544/25; 544/24; 544/21
[58] Field of Search ...................... 544/25, 24, 21, 22, 544/28, 30; 424/246

[56] References Cited

U.S. PATENT DOCUMENTS 4,080,498  3/1978  Numaca et al. ...................... 544/27
4,098,888  7/1978  Ochiai et al. ......................... 544/27
4,387,096  6/1983  DiSchiena et al. ................... 544/25

Primary Examiner—Nicholas S. Rizzo
Attorney, Agent, or Firm—Sprung, Horn, Kramer & Woods

[57] ABSTRACT

Antibacterially active cephalosporins of the formula

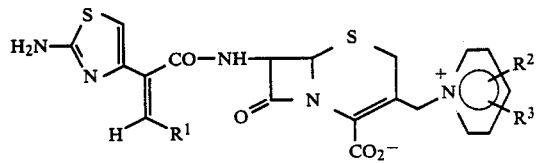

in which $R^1$ denotes $C_1$–$C_6$-alkyl, phenyl or halogen-substituted phenyl, and $R^2$ and $R^3$, which can be identical or different, denote H, $C_1$–$C_4$-alkyl, chlorine, bromine, carbamoyl or N-$C_1$–$C_4$-alkylcarbamoyl.

12 Claims, No Drawings

CEPHALOSPORINS

The invention relates to new cephalosporins, their use as medicaments, in particular in antibacterial therapy, and a process for their preparation.

The invention makes available cephalosporins of the general formula I.

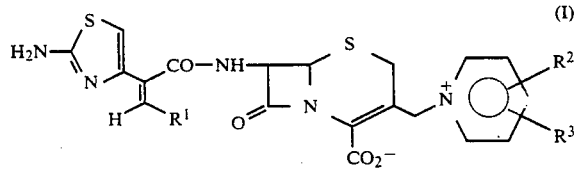

In the general formula I, $R^1$ denotes $C_1$-$C_6$ alkyl, phenyl or halogen-substituted phenyl, and $R^2$ and $R^3$ are identical or different and denote H, $C_1$-$C_4$—alkyl, chlorine, bromine, carbamoyl or N—$C_1$—$C_4$-alkylcarbamoyl.

Preferred compounds are those in which $R^1$ = $C_1$-$C_5$ alkyl and $R^2$ = H, $C_1$-$C_2$—alkyl, carbamoyl, chlorine or bromine.

A very particularly preferred compound is that in which $R^1$ = $CH_3$ and $R^2$ and $R^3$ = H.

The compounds of the formula I are obtained by a process wherein the acids of the formula II, wherein $R^4$ represents a customary protective group, are converted to the mixed anhydrides of the formula III, and these are reacted with the known compounds of the formula IV, and the protective group $R^4$ is then split off from the resulting compounds of the formula V.

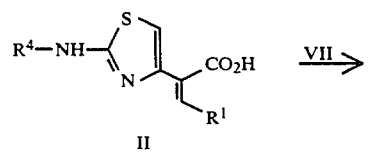

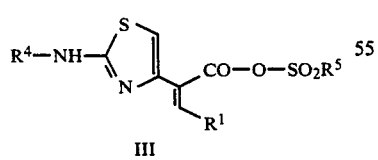

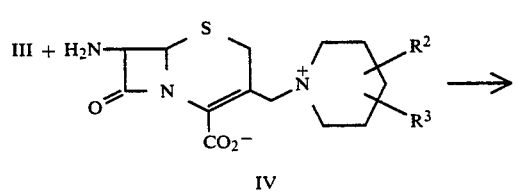

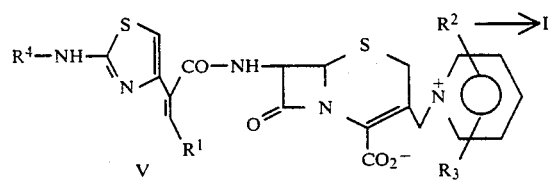

It is advantageous for the process to use, as $R^4$, a protective group, such as, for example, tert.-butoxycarbonyl, trityl or formyl, which is unstable to acids, and to split off $R^4$ in V with, for example, trifluoroacetic acid or formic acid.

Furthermore, it is advantageous to choose $CH_3$ for $R^5$.

The compounds II and III can be prepared according to the following equation.

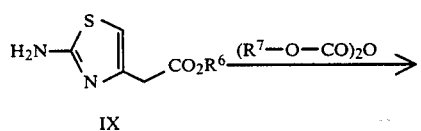

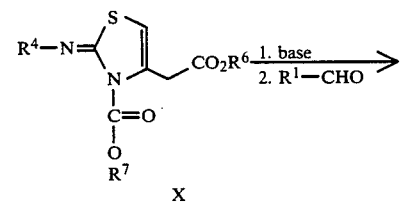

(In this process for the preparation of II, $R^4$ is $R^7$—O—CO)

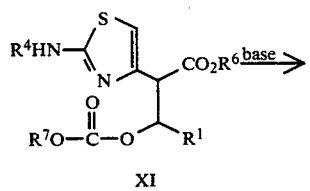

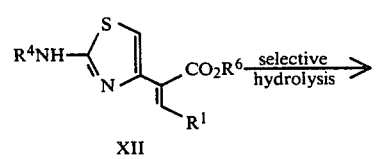

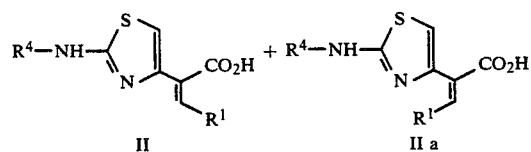

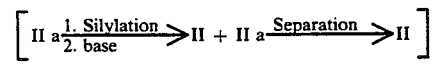

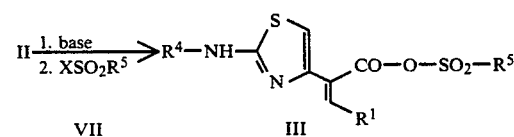

First, the compounds of the formula IX (see, for example, E. Campaigne and T. P. Selby, J. Heterocycl. Chem. 17 (1980), 1255) are converted to the compounds of the formula X.

The meanings are as follows:

$R^4$ is an amine protective group, such as, for example, acetyl, benzoyl, formyl, trichloroacetyl, benzyloxycarbonyl, methoxycarbonyl or tert.-butoxycarbonyl, $R^6$ and $R^7$ can be identical or different and can denote an optionally substituted alkyl, cycloalkyl, alkenyl, cycloalkenyl, aryl or heterocyclyl radical, and hetero atoms as substituents of the radicals, and double bonds in the alkenyl and cycloalkenyl radicals, are separated from the oxycarbonyl group by at least 1 carbon atom.

In particular $R^6$ and $R^7$ are an optionally substituted alkyl radical having 1-15 carbon atoms, an optionally substituted alkenyl radical having 3-15 carbon atoms, an optionally substituted cycloalkyl radical having 3-10 carbon atoms, an optionally substituted cycloalkenyl radical having 5-10 carbon atoms, an optionally substituted aryl radical having 1 to 3 rings or an optionally substituted heterocyclyl radical which has 1-3 rings and which can contain up to 5 nitrogen, sulphur or oxygen atoms.

The stated alkyl, alkenyl, cycloalkyl and cycloalkenyl radicals can be substituted by alkyl radicals having 1-4 carbon atoms, O-alkyl radicals having 1-4 carbon atoms, halogen, preferably chlorine, optionally substituted phenyl radicals, $C\equiv N$ and C1-C5-trialkylsilyl.

All aryl and heterocyclyl radicals, including the stated phenyl radicals, can be substituted by alkyl, O-alkyl, S-alkyl, alkoxycarbonyl, halogen, phenyl, nitro and $C\equiv N$ radicals, it being possible for all alkyl radicals to have 1 to 4 carbon atoms.

If the radicals $R^6$ and/or $R^7$ are substituted, preferably by the abovementioned substituents, they can carry 1-5, preferably 1 or 2, substituents.

It is particularly advantageous for the process if $R^4$ is a protective group, such as, for example, tert.-butoxycarbonyl, which is stable to bases and can be split off in acids, and if $R^6$ is a radical, such as, for example, methyl or ethyl, which can be hydrolyzed in a basic medium.

The compounds of the formula X are obtained by allowing the compounds of the formula IX, which are in themselves known, to react with a pyrocarbonate of the formula $R^7-O-CO-O-CO-O-R^7$, in a suitable solvent.

Particularly suitable solvents are aprotic, polar solvents, such as, for example, acetonitrile, dimethylformamide, hexamethylphosphoric acid triamide and dimethylsulphoxide, particularly the two last-mentioned. The reaction is particularly advantageously carried out at room temperature or at low temperatures, for example 0° to −50° C., and the components are allowed to react with one another for 1-7 days. In general 2-2.5 mol-equivalents of the pyrocarbonate are employed.

To prepare the compounds of the formula XI, 1 to 1.1 equivalents of a base are added to the compounds of the formula X in a suitable solvent at low temperatures, and 1 to 1.2 equivalents of an aldehyde of the formula $R^1$—CHO are then added.

Examples of solvents which can be used for the reaction are dimethylformamide, dimethylsulphoxide, diethyl ether, tetrahydrofuran and toluene, preferably tetrahydrofuran, and bases which can be used are alcoholates, hydrides, amides and organometallic compounds, preferably potassium tert.-butylate, lithium diisopropylamide and butyl-lithium. To carry out the reaction, the base is added to a solution of X at −50° to −80° C. and the aldehyde is then added at −50° to −60° C., and the mixture is stirred for approx. 12 hours at −50° to −60° C. To isolate the products of the formula XI, the mixture is neutralized and worked up.

In the compounds of the formula XI, $R^4$, $R^6$ and $R^7$ have the meanings listed in the case of the compounds of the formula X, and $R^1$ has the meaning mentioned at the outset.

To carry out the process for the preparation of the compounds of the formula I, it is not necessary to isolate the compounds of the formula XI. Instead, it is advantageous to convert them in situ directly to the compounds of the formula XII. To do this, it is generally sufficient to allow the mixture to warm up to room temperature after the aldehyde $R^1$—CHO has been added, and to stir the mixture overnight at room temperature. If by this time conversion of XI to XII is not complete, 1 to 1.2 equivalents of a base, such as, for example, a hydride, an alcoholate or an amide, in particular potassium tert.-butylate, are added, and the mixture is stirred for about 10 hours at room temperature.

If, on the other hand, the compound of the formula XI has been isolated beforehand, the compounds of the formula XII are prepared by adding 1.1 to 2.2 equivalents of a base to a solution of the compounds of the formula XI in a suitable solvent. Solvents and bases which can be used are those mentioned for the conversion of X to XI, preferably tetrahydrofuran and potassium tert.-butylate.

The compounds of the formula XII are obtained as E/Z-isomer mixtures, which can be separated, for example, by recrystallization or column chromatography over silica gel.

In the compounds of the formula XII, $R^1$, $R^4$ and $R^6$ have the same meaning as in the compounds of the formula XI.

To prepare the Z-carboxylic acids of the formula II the Z-esters, which can be obtained by separation of the E/Z-isomer mixtures of the esters of the formula XII, can be hydrolyzed. However, the process for the preparation of the compounds of the formula I can be carried out more advantageously if the E/Z-isomer mixture of the esters of the formula XII is selectively hydrolyzed in a manner such that first the E-esters are converted to the E-carboxylic acids of the formula II a under mild conditions and the products are separated off, and thereafter the remaining Z-esters, in which the ester group is sterically protected to a greater extent, are hydrolyzed under drastic conditions to give the Z-carboxylic acids of the formula II.

The mild hydrolysis conditions which lead to the E-carboxylic acids II a are, for example, ethanol/2N sodium hydroxide solution/room temperature/ 24 hours. The hydrolysis is advantageously carried out in a manner such that, after conversion of the compounds of the formula XI to the compounds of the formula XII, 2N sodium hydroxide solution is added directly to the reaction mixture, and the mixture is stirred at room temperature, or while warming slightly, until the E-esters are hydrolyzed. Thereafter, the Z-esters are separated off from the mixture by extraction in an alkaline medium, and are hydrolyzed under more drastic conditions.

More drastic hydrolysis conditions are, for example, ethanol/2N sodium hydroxide solution/refluxing for 24 hours—if necessary, even stronger sodium hydroxide solution or higher-boiling solvents, such as, for example, dioxane.

In this manner, the desired Z-carboxylic acids of the formula II an the E-carboxylic acids of the formula II a are obtained. The latter can be converted to the silyl esters, for example with bistrimethylsilylacetamide, and these can be converted, in a suitable solvent, for example diethyl ether or tetrahydrofuran, by means of a base, such as potassium tert.-butylate, and subsequent hydrolysis with dilute acid, to a mixture of the E-carboxylic acids of the formula II a and the Z-carboxylic acids of the formula II.

From this E/Z-isomer mixture, the Z-carboxylic acids of the formula II can be isolated in pure form by crystallization or by separation over an ion exchanger.

Separation with the aid of ion exchangers is simple since the Z-carboxylic acids of the formula II are very much more strongly acidic than the E-carboxylic acids of the formula II a. Thus, it is even possible to use methanol to elute the E-carboxylic acids of the formula II a from weakly basic ion exchangers, but the Z-carboxylic acids of the formula II are eluted only after the addition of electrolytes, for example 2N sodium hydroxide solution. Weakly basic ion exchangers are to be understood as meaning those ion exchangers in solid or liquid form which contain tertiary amino groups, such as, for example, Lewatit MP 62.

In the compounds of the formula II and II a, $R^1$ and $R^4$ have the same meaning as in the compounds in the formula XII. In addition, $R^4$ can be H if, in the compounds of the formula XII, before hydrolysis, $R^4$ was a protective group, such as, for example, acetyl, which can be hydrolyzed by an alkali. However, to carry out the process for the preparation of the compounds of the formula I, it is more advantageous if $R^4$ is a protective group which is stable under the hydrolysis conditions—preferably tert.-butoxycarbonyl.

In cephalosporin chemistry, a large number of methods, which in the end are derived from peptide chemistry, are known for coupling carboxylic acids to 7-aminocephalosporanic acids. However, in attempts to form the amide bond between the Z-carboxylic acids of the formula II and the cephalosporanic acids of the formula IV, these methods are unsuccessful or only lead to very poor yields, particularly when $R^1$ is an alkyl radical. The reasons for this lie in the high degree of steric hindrance of the carboxyl group in the carboxylic acids of the formula II by the radical $R^1$, and in the pronounced tendency of the radical $R^1$, after activation of the carboxyl function, for example conversion to the acid chloride, to undergo isomerization to the E form.

However, the Z-carboxylic acids of the formula II can be activated in a simple, gentle and cheap manner if they are converted at low temperatures to the mixed anhydrides of the formula III.

Such mixed anhydrides of the formula III can be prepared by dissolving the carboxylic acid II and a suitable amine in equimolar amounts in a suitable solvent, and allowing them to react with 1 to 1.05 equivalents of a sulphonic acid derivative of the formula VII.

Suitable solvents are all solvents which are stable under the reaction conditions, such as, for example, diethyl ether, tetrahydrofuran, acetonitrile, acetone, methylene chloride, chloroform or dimethylformamide.

Suitable amines are tertiary amines, such as, for example, triethylamine or tributylamine, as well as sterically hindered secondary amines, such as, for example, diisopropylamine.

The reactions can be carried out at temperatures between −80° C. and room temperature, and low temperatures avoid isomerization of the substituents at the double bond. The reactions are advantageously carried out at −20° to −50° C. for a reaction time of 10 minutes to 10 hours.

The compounds of the formula III can be isolated by using, for example, tetrahydrofuran as a solvent and triethylamine as a base, filtering off the resulting triethylamine hydrochloride, and distilling off the solvent in vacuo. However, it is more advantageous to react the resulting solutions of the compounds of the formula III directly with the cephalosporanates of the formula IV. For this purpose, the cephalosporanates of the formula IV or their salts are dissolved in a suitable solvent with 1-4 equivalents of an amine, the solution is pre-cooled to the desired subsequent reaction temperature, and this solution is added, at this temperature, to the solution of the compound of the formula III described above. To avoid isomerization of the radical $R^1$ in the reaction products of the formula V, the reaction is advantageously carried out at −60° to −30° C. and the mixture is allowed to reach room temperature overnight.

To dissolve the compounds of the formula IV, it is possible to use the solvents mentioned in the case of the preparation of the compounds of the formula III, and, as the base, to use the amines mentioned in that connection.

In general, the solubility of the compounds of the formula IV in the solvents is very limited, so that it is advantageous in this case to carry out silylation in a manner which is in itself known, or to employ water as a solvent.

It is particularly advantageous to convert the carboxylic acids VI, without a protective group and using the sulphonic acid derivatives VII, to the mixed anhydrides of the formula VIII, and to react these directly with IV to give the compounds of the formula I.

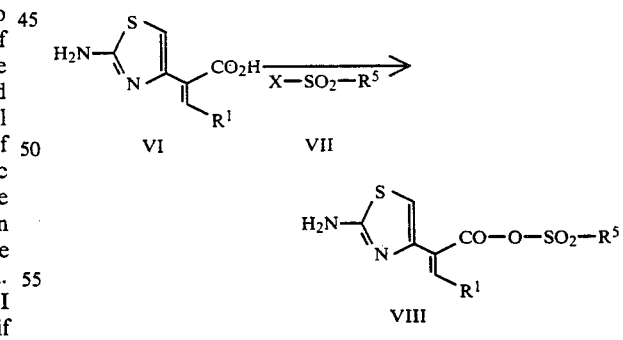

X denotes Cl, Br or $OSO_2R^5$ and $R^5$ denotes an alkyl radical which has 1–10 carbon atoms and can be optionally substituted by fluorine, chlorine, CN, phenyl, alkoxycarbonyl, alkoxy or alkyl, it being possible for the latter alkyl radicals to carry 1–4 carbon atoms, or denotes a phenyl radical which can be optionally substituted by fluorine, chlorine, bromine, CN, alkyl, alkoxy, alkylthio, alkoxycarbonyl—it being possible for the latter alkyl groups to carry 1-4 carbon atoms—nitro, trifluoromethyl and phenyl.

If $R^5$ is substituted, preferably 1-3 substituents, preferably those mentioned, are present.

$R^5$ very particularly preferably represents a methyl or p-tolyl radical.

The mixed anhydrides of the formula VIII are prepared analogously to the anhydrides of the formula III, by dissolving the carboxylic acids of the formula VI and 1-1.4 equivalents of an amine in a solvent, and allowing them to react with 1.2 equivalents of a sulphonic acid derivative of the formula VII.

Suitable solvents are all solvents which are stable under the reaction conditions, such as, for example, diethyl ester, tetrahydrofuran, acetonitrile, acetone, methylene chloride, chloroform or dimethylformamide.

Suitable amines are tertiary amines, such as, for example, triethylamine or tributylamine, as well as sterically hindered secondary amines, such as, for example, diisopropylamine.

The reactions can be carried out at temperatures between $-80°$ C. and room temperature, and low temperatures avoid isomerization of the substituents at the double bond. Advantageously, the reaction with Cl—$SO_2CH_3$ is carried out in dimethylformamide at $-40°$ to $-60°$ C.

To dissolve the compounds of the formula IV, the solvents mentioned in the case of the preparation of the compounds of the formula VIII can be used, and the amines mentioned in that connection can be used as bases.

In general, the solubility of the compounds of the formula IV in the solvents is very limited, so that it is advantageous in this case to carry out silylation in a manner which is in itself known, or to employ water as a solvent.

The compounds of the formula VI are obtained by splitting off the protective group $R^4$ from the compounds of the formula II—for example the Boc protective group with trifluoroacetic acid.

A further process for the preparation of the compounds of the formula I is the reaction of cephalosporins of the formula XII with pyridines of the formula XIII, wherein

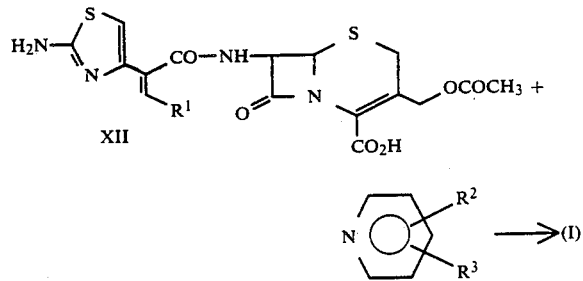

$R^1$-$R^3$ have the meaning mentioned in the case of the compounds of the formula 1. The reaction is carried in a polar organic solvent, such as, for example, dimethylformamide, or in water—preferably in water with an excess of pyridine—in general 10 equivalents, at temperatures between 40° and 95° C. and for reaction times between 5 minutes and 6 hours. To isolate the products of the formula I, it is advantageous, after extraction of the pyridine, to chromatograhp the resulting crude product over a resin, such as, for example, Diaion HP 20 or XAD 7, or even over cellulose.

The compounds of the formula XII can be obtained in an analogous manner to the compounds according to the invention, of the formula I. For this purpose, it is merely necessary, in the coupling of the compounds of the formula VIII, to employ 7-aminocephalosporanic acid instead of the cephalosporanate of the formula IV.

The compounds according to the invention possess a powerful and broad antimicrobial activity, particularly against gram-negative and gram-positive bacteria. These properties make it possible to use them as chemotherapeutic active compounds in medicine. With their aid it is possible to prevent, alleviate and/or cure diseases caused by gram-negative and gram-positive bacteria and bacteria-like micro-organisms.

The compounds according to the invention are particularly active against bacteria and bacteria-like microorganisms. They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermis* and *Staph. aerogenes* and *Gaffkya tetragena* (Staph.=Staphylococcus); Lactobacteriaceae, such as Streptococci, for example *Streptococcus pyogenes*, α- and β- haemolysing Streptococci, non-(γ-)-haemolysing Streptococci, *Str. viridans, Str. faecalis* (Enterococci) and *Diplococcus pneumoniae* (pneumococci) (Str.=Streptococcus); Enterobacteriaceae, such as Escherichiae bacteria of the Coli group: Escherichia bacteria, for example *Escherichia coli*, Enterobacter bacteria, for example *E. aerogenes* and *E. cloacae*, Klebsiella bacteria, for example *K. pneumoniae*, Serratia, for example *Serratia marvescens* (E.=Enterobacter) (K.=Klebsiella), and Proteae bacteria of the Proteus group: Proteus, for example *Proteus vulgaris, Pr. morganii, Pr. rettgeri* and *Pr. mirabilis,* (Pr.=Proteus); Pseudomonadaceae, such as Pseudomonas bacteria, for example *Pseudomonas aeruginosa* (Ps.=Pseudomonas); and Bacteroidaceae, such as Bacteroides bacteria, for example . *Bacteroides fragilis* (B.=Bacteroides).

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis; arthritis; and local infections.

The present invention includes pharmaceutical formulations which, in addition to non-toxic, inert pharmaceutically suitable excipients, contain one or more compounds according to the invention, or which consist of one or more active compounds according to the invention, as well as processes for the preparation of these formulations.

The present invention also includes pharmaceutical formulations in dosage units. This means that the formulation are in the form of individual parts, for example tablets, dragees, capsules, pills, suppositories and ampules, of which the content of active compound correspond to a fraction or a multiple of an individual dose. The dosage units can contain, for example, 1, 2, 3 or 4 individual doses of ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resoprtion accelerators, for example quaternary ammonium compounds, (g) wetting agents, for example cetyl alcohol and glycerol monostearate, (h) adsorbents, for example kaolin and bentonite, and (i) lubricants, for example talc, calcium and mgnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

For parenteral administration, the solutions can also be in a sterile form which is isotonic with blood.

The therapeutically active compounds should preferably be present in the abovementioned pharmaceutical formulations in a concentration of about 0.1 to 99.5, preferably of about 0.5 to 95 percent by weight of the total mixture.

The abovementioned pharmaceutical formulations can also contain other pharmaceutically active compounds in addition to the compounds according to the invention.

The abovementioned pharmaceutical formulations are prepared in the customary manner according to known methods, for example by mixing the active compound or compounds with the excipient or excipients.

The active compounds or the pharmaceutical formulations can be administered locally, orally, parenterally, intraperitoneally and/or rectally, preferably orally of parenterally, such as intravenously or intramuscularly.

In general, it has proved advantageous both in human medicine and in veterinary medicine, to administer the active compound or compounds according to the invention in total amounts of about 1 to 1,000, preferably 1 to 200 mg/kg of body weight every 24 hours, optionally in the form of several individual administrations, in order to achieve the desired results. An individual administration preferably contains the active compound or compounds according to the invention in amounts of about 1 to about 250, in particular 1 to 60, mg/kg of body weight. However, it can be necessary to deviate from the dosages mentioned, and in particular to do so as a further function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, while in other cases the abovementioned amount of active compound must be exceeded. The particular optimum dosage required and the type of administration of the active compounds can easily be determined by anyone skilled in the art on the basis of his expert knowledge.

In order to broaden the spectrum of action, the compounds according to the invention can be combined with another β-lactam antibiotic or even with aminoglycoside antibiotics, such as, for example, gentamicin, sisomicin, kanamicin, amikacin or tobramicin.

EXAMPLES 1. 7-[1-(2-tert.-butoxycarbonylaminothiazol-4-yl)-1(Z)-propenecarboxamido]-3-pyridiniummethyl-3-cephem-4-carboxylate 5 millimols (1.42 g) of 1-(2-tert.-butoxycarbonylaminothiazol-4-yl)-1(Z)-propenecarboxylic acid and 5.5 millimols (0.76 ml) of triethylamine were dissolved in 30 ml of anhydrous dimethylformamide, the solution was cooled to −55° C., 5.1 millimols (0.4 ml) of methanesulphonic acid-chloride were added, and the mixture was stirred for half an hour at −55° C.

The solution thus prepared, at −55° C., was poured, in one portion, onto a solution of 4 millimols (1.16 g) of 7-amino-3-pyridiniummethyl-3-cephem-4-carboxylate and 4 millimols (0.55 ml) of triethylamine in 2 ml of water, the mixture was allowed to warm up to room temperature and the pH was kept at 8–9.5 with triethylamine during this procedure.

After 30 minutes, the mixture was evaporated down in vacuo in a rotary evaporator, the residue was dissolved in a small amount of water, the pH was adjusted to 3–4, the solution was extracted with ethyl acetate, and the aqueous solution was lyophilized.

2. 7-[1-(2-tert.-butoxycarbonylaminothiazol-4-yl)-1(Z)-butenecarboxamido]-3-pyridiniummethyl-3-cephem-4-carboxylate The preparation was carried out analogously to Example 1, from 1-(2-tert.-butoxycarbonylaminothiazol-4-yl)-1(Z)-butenecarboxylic acid.

3. 7-[1-(2-tert.-butoxycarbonylaminothiazol-4-yl)-1(Z)-pentenecarboxamido]-3-pyridiniummethyl-3-cephem-4-carboxylate The preparation was carried out analogously to Example 1, from 1-(2-tert.-butoxycarbonylaminothiazol-4-yl)-1(Z)-pentenecarboxylic acid.

4. 7-[1-(2-tert-butoxycarbonylaminothiazol-4-yl)-1(Z)-heptenecarboxamido]-3-pyridiniummethyl-3-cephem-4-carboxylate The preparation was carried out analogously to Example 1, from 1-(2-tert.-butoxycarbonylaminothiazol-4-yl)-1(Z)-heptene-carboxylic acid.

5. 7-[1-(2-tert.-butoxycarbonylaminothiazol-4-yl)-1(Z)-propenecarboxamido]-3-(4-aminocarbonylpyridinium-methyl)-3-cephem-4-carboxylate The preparation was carried out analogously to Example 1, from 1-(2-tert.-butoxycarbonylaminothiazol-4-yl)-1(Z)-propenecarboxylic acid and 7-amino-3-(4-aminocarbonylpyridiniummethyl)-3-cephem-4-carboxylate.

6a. 7-[1-(2-aminothiazol-4-yl)-1(Z)-propenecarboxamido]-3-pyridiniummethyl-3-cephem-4-carboxylate 41 millimols (7.5 g) of 1-(2-aminothiazol-4-yl)-1(Z)-propenecarboxylic acid and 45 millimols (6.3 ml) of triethylamine were dissolved in 200 ml of anhydrous dimethylformamide, the solution was cooled to −55° C., 42 millimols (3.3 ml) of methanesulphonic acid-chloride were added, and the mixture was stirred for 30 minutes at −55° C.

Thereafter, the solution, at −55° C., was poured, in one portion, onto a solution of 31 millimols (11.2 g) of 7-amino-3-pyridiniummethyl-3-cephem-4-carboxylate and 31 millimols (4.3 ml) of triethylamine in 20 ml of water, and the mixture was allowed to warm up to room temperature while stirring vigorously, the pH being kept at 8–9.5 with triethylamine.

To work up the mixture, it was evaporated down in vacuo in a rotary evaporator, and the residue was trituated with ether and washed several times with methylene chloride and acetone.

To remove residual salts and impurities, the product was purified by chromatography over cellulose with acetonitrile/water 5:1, or by absorption on, for example, Diaion HP 20 or XAD 7 and desorption with water/acetone 90:10. Yield 10.5 g.

6b. 7-[1-(2-aminothiazol-4-yl)-1(Z)-propenecarboxamido]-3-pyridiniummethyl-3-cephem-4-carboxylate 41 millimols (7.5 g) of 1-(2-aminothiazol-4-yl)-1(Z)-propenecarboxylic acid and 45 millimols (7.8 ml) of ethyl-di-isopropylamine were dissolved in 100 ml of anhydrous dimethylformamide, the solution was cooled to −55° C., 42 millimols (3.3 ml) of methanesulphonic acid-chloride were added, and the mixture was stirred at −55° C.

Thereafter, the solution, at −55° C., was poured, in one portion, onto a vigorously stirred solution of 31 millimols (11.2 g) of 7-amino-3-pyridinium-methyl-3-cephem-4-carboxylate in 12 ml of water, 31 millimols (4.3 ml) of triethylamine were added simultaneously and the mixture was allowed to warm up to room temperature, the pH being kept at 8.5–9.5 with triethylamine.

To work up the mixture, it was stirred into 1.5 liters of acetone after 10–20 minutes, and the precipitate was filtered off under suction and washed several times with methylene chloride and acetone.

To remove residual salts and impurities, the product was purified by chromatography over cellulose with acetonitrile/water 5:1, or by absorption on, for example, Diaion HP 20 or XAD 7 and desorption with water/acid 90:10.

Yield: 10.5 g.

7. 7-[1-(2-aminothiazol-4-yl)-1(Z)-propenecarboxamido]-3-pyridiniummethyl-3-cephem- 4-carobxylate The product from Example 1 was stirred with 20 ml of trifluoroacetic acid for 2 hours at room temperature, the mixture was evaporated down in vacuo in a rotary evaporator, the residue was trituated with ether, an the product was filtered off under suction, washed with triethylamine-containing methylene chloride, methylene chloride and acetone, and purified as stated in Example 6.

8. 7-[1-(2-aminothiazol-4-yl)-1(Z)-butenecarboxamido]-3-pyridiniummethyl-3-cephem-4-carboxylate To prepare the compound, the product from Example 2 was converted analogously to Example 7.

9. 7-[1-(2-aminothiazol-4-yl)-1(Z)-pentenecarboxamido]-3-pyridiniummethyl-3-cephem-4-carboxylate To prepare the compound, the product from Example 3 was converted analogously to Example 7.

10. 7-[1-(2-aminothiazol-4-yl)-1(Z)-heptenecarboxamido]-3-pyridiniummethyl-3-cephem-4-carboxylate To prepare the compound, the product from Example 4was converted analogously to Example 7.

11. 7-[1-(2-aminothiazol-4-yl)-1(Z)-propenecarboxamido]-3-(4-aminocarbonylpyridiniummethyl)-3-cephem-4-carboxylate To prepare the compound, the product from Example 5 was converted analogously to Example 7.

12. 1-(2-aminothiazol-4-yl)-1(Z)-propenecarboxylic acid 50 g (0.176 mol) of 1-(2-tert.-butoxycarbonylaminothiazol-4-yl)-1(Z)-popenecarboxylic acid and 350 ml of trifluoroacetic acid were combined at 0° C., and the mixture was stirred to 3 hours at room temperature. The trifluoroacetic acid was stripped in vacuo, a saturated aqueous $NaHCO_3$ solution was added to the residue until the pH was 2, followed by the addition of saturated aqueous $KHCO_3$ solution until the pH was 3.7–4.0, the residue being stirred and cooled with ice. The precipitate was filtered off under suction, washed with water and dried in vacuo over $P_2O_5$.

Yield 29.5 g (91%).

13. 7-[1-(2-aminothiazol-4-yl)-1(Z)-propencarboxamido]-3-(2-methylpyridinium)methyl-3-cephem-4-carboxylate This compound was made in analogy to example 6 from 3 mmol (552 mg) 1-(2-aminothiazol-4-yl)-1(Z)-propenecarboxylic acid and 3 mmol (915 mg) 7-amino-3-(2-methylpyridinium)methyl-3-cephem-4-carboxylate. For work-up the mixture was poured into 450 ml acetone, the precipitation was succed off and purified by absorption on Diaion HP 20 and desorption with water/acetnoitrile 9:1.

Yield: 377 mg.

$^1$H-NMR (D$_6$-DMSO)

$\delta$=9.35 (1H, d, J=6 Hz, H-6-Py); 9.19 (1H, d, J=8 Hz, NH); 8.42 (1H, m, H-4-Py); 7.97 (2H, m, H-3,5-Py); 6.98 (2H, bs, NH$_2$); 6.37 (1H, q, J=8 Hz, C=CH); 6.18 (1H, s, thiazol); 5.66 (1H, dd, J=8 Hz, J=5 Hz, H-7-lactam); 5.39 (2H, bs, CH$_2$-Py); 5.07 (1H, d, J=5 Hz, H-6-lactam); 3.42 (1H, d, J=18 Hz, S-CH$_2$); 3.09 (1H, d, J=18 Hz, S-CH$_2$); 2.84 (2H, s, Py-CH$_3$); 1.75 (3H, d, J=8 Hz, C=C—CH$_3$).

14. 7-[1-(2-aminothiazol-4-yl)-1(Z)-propencarboxamido]-3-(3-methylpyridinium)methyl-3-cephem-4-carboxylate The preparation was in analogy to example 13 from 7-amino-3-(3-methylpyridinium)methyl-3-cephem-4-carboxylate.

Yield: 370 mg.

$^1$H-NMR (D$_6$-DMSO)

δ=9.42 (1H, d, J=5 Hz, H-6-Py); 9.29 (1H, s, H-2-Py); 9.18 (1H, d, J=7 Hz, NH); 8.42 (1H, d, J=8 Hz, H-4-Py); 8.06 (1H, m, H-5-Py); 6.98 (2H, bs, NH$_2$); 6.38 (1H, q, J=8 Hz, C=CH); 6.17 (1H, s, thiazol); 5.65 (2H, m, H-7-lactam, CH$_2$-Py); 5.09 (1H, d, J=5 Hz, H-6-lactam); 5.06 (1H, d, J=15 Hz, CH$_2$-Py); 3.55 (1H, d, J=18 Hz, S-CH$_2$); 3.08 (1H, d, J=18 Hz, S-CH$_2$); 2.48 (3H, s, Py-CH$_3$); 1.75 (3H, d, J=8 Hz; C=C—CH$_3$).

15. 7-[1-(2-aminothiazol-4-yl)-1(Z)-propencarboxamido]-3-(4-methylpyridinium)methyl-3-cephem-4-carboxylate The preparation was in analogy to example 13 from 7-amino-3-(4-methylpyridinium)methyl-3-cephem-4-carboxylate.

Yield: 360 mg.

$^1$H-NMR (D$_6$-DMSO)

δ=9.33 (2H, d, J=6 Hz, H-2,6-Py); 9.20 (1H, d, J=8 Hz, NH); 7.99 (2H, d, J=6 HZ, H-3,5-Py); 6.98 (2H, bs, NH$_2$); 6.30 (1H, q, J=8 Hz, C=CH); 6.18 (1H, s, thiazol); 5.68 (1H, dd, J=8 Hz, J=5 Hz, H-7-lactam); 5.61 (1H, d, J=15 Hz, CH$_2$-Py); 5.11 (1H, d, J=5 Hz, H-6-lactam); 5.03 (1H, d, J=15 Hz, CH$_2$-Py); 3.55 (1H, d, J=18 Hz, S-CH$_2$); 3.04 (1H, d, J=18 Hz, S-CH$_2$); 2.60 (3H, s, Py-CH$_3$); 1.76 (3H, d, J=8 Hz, C=C—CH$_3$).

16. 7-[1-(2-aminothiazol-4-yl)-1(Z)-propencarboxamido]-3-(4-ethylpyridinium)methyl-3-cephem-4-carboxylate This compound was made in analogy to example 16 from 7-amino-3-(4-ethylpyridinium)methyl-3-cephem-4-carboxylate.

Yield: 140 mg.

$^1$H-NMR (D$_6$-DMSO)

δ=9.35 (2H, d, J=6 Hz, H-2,6-Py); 9.18 (1H, d, J=9 Hz, NH); 8.03 (2H, d, J=6 Hz, H-3,5-Py); 6.98 (2H, bs, NH$_2$); 6.29 (1H, q, J=8 Hz, C=CH); 6.18 (1H, s, thiazol); 5.68 (1H, dd, J=9 Hz, J=5 Hz, H-7-lactam); 5.61 (1H, d, J=15 Hz, CH$_2$-Py); 5.10 (1H, d, J=5 Hz, H-6-lactam); 5.05 (1H, d, J=15 Hz, CH$_2$-Py); 3.54 (1H, d, J=18 Hz, S-CH$_2$); 3.04 (1H, d, J=18 Hz, S-CH$_2$); 2.89 (2H, q, J=6 Hz, Py-CH$_2$-CH$_3$); 1.75 (3H, d, J=8 Hz, C=C—CH$_3$); 1.26 (3H, t, J=6 Hz, Py-CH$_2$-CH$_3$).

17. 7-[1-(2-aminothiazol-4-yl)-1(Z)-porpencarboxamido]-3-(2,3-dimethylpyridinium)methyl-3-cephem-4-carboxylate Preparation in analogy to example 13 from 7-amino-3-(2,3-dimethylpyridinium)methyl-3-cephem-4-carboxylate.

Yield: 280 mg.

$^1$H-NMR (D$_6$-DMSO)

δ=9.19 (1H, d, J=9 Hz, NH); 9.16 (1H, d, J=6 Hz, H-6-Py); 8.29 (1H, d, J=8 Hz, H-4-Py); 7.88 (1H, m, H-5-Py); 6.98 (2H, bs, NH$_2$); 6.27 (1H, 9, J=8 Hz, C=CH); 6.17 (1H, s, thiazol); 5.65 (1H, dd, J=9 Hz, J=5 Hz, H-7-lactam); 5.38 (2H, bs, CH$_2$-Py); 5.07 (1H, d, J=5 Hz, H-6-lactam); 3.42 (1H, d, J=18 Hz, S-CH$_2$); 3.07 (1H, d, J=18 Hz, S-CH$_2$); 2.74 (3H, s, Py-2-CH$_3$); 2.40 (3H, s, Py-3-CH$_3$); 1.75 (3H, d, J=8 Hz, C=C—CH$_3$).

18. 7-[1-(2-aminothiazol-4-yl)-1-(Z)-propencarboxamido]-3-(2,4-dimethylpyridinium)methyl-3-cephem-4-carboxylate Preparation in analogy to example 13 from 7-amino-3-(2,4-dimethylpyridinum)methyl-3-cephem-4-carboxylate.

Yield: 320 mg.

$^1$H-NMR (D$_6$-DMSO)

δ=9.20 (1H, d, J=9 Hz, NH); 9.17 (1H, d, J=6 Hz, H-6-Py); 7.83 (1H, s, H-3-Py); 7.81 (1H, d, J=6 Hz, H-5-Py); 6.98 (2H, bs, NH$_3$); 6.28 (1H, q, J=8 Hz, C=CH); 6.17 (1H, s, thiazol); 5.65 (1H, dd, J=9 Hz; J=5 Hz, H-7-lactam); 5.31 (2H, bs, CH$_2$-Py); 5.05 (1H, d, J=5 Hz, H-6-lactam); 3.40 (1H, d, J=18 Hz, S-CH$_2$); 3.05 (1H, d, J=18 Hz, S-CH$_2$); 2.75 (3H, s, Py-2-CH$_3$); 2.50 (3H, s, Py-4-CH$_3$); 1.75 (3H, d, J=8 Hz, C=C—CH$_3$).

19. 7-[1-(2-aminothiazol-4-yl)-1-(Z)-propencarboxamido]-3-(3,4-dimethylpyridinium)methyl-3-cephem-4-carboxylate Preparation in analogy to example 16 from 7-amino-3-(3,4-dimethylpyridinium)methyl-3-cephem-4-carboxylate.

Yield: 200 mg.

$^1$H-NMR (D$_6$-DMSO)

δ=9.20 (3H, m, NH, H-2,6-Py); 7.95 (1H, d, J=6 Hz, H-5-Py); 6.98 (2H, bs, NH$_2$); 6.29 (1H, q, J=8 Hz, C=CH); 6.18 (1H, s, thiazol); 5.66 (1H, dd, J=9 Hz, J=5 Hz, H-7-lactam); 5.58 (1H, d, J=15 Hz, CH$_2$-Py); 5.09 (1H, d, J=5 Hz, H-6-lactam); 5.00 (1H, d, J=15 Hz, CH$_2$-Py); 3.52 (1H, d, J=18 Hz, S-CH$_2$); 3.05 (1H, d, J=18 Hz, S-CH$_2$); 2.50 (3H, s, Py-4-CH$_3$); 2.36 (3H, s, Py-3-CH$_3$); 1.75 (3H, d, J=8 Hz, C=C—CH$_3$).

20. 7-[1-(2-aminothiazol-4-yl)-1(Z)-propencarboxamido]-3-(3,5-dimethylpyridinium)methyl-3-cephem-4-carboxylate Preparation in analogy to example 16 from 7-amino-3-(3,5-dimethylpyridinium)methyl-3-cephem-4-carboxylate.

Yield: 220 mg.

$^1$H-NMR(D$_6$-DMSO)

δ=9.20 (2H, s, H-2,6-Py); 9.18 (1H, d, J=9 Hz, NH); 8.27 (1H, s, H-4-Py); 6.97 (2H, bs, NH$_2$); 6.28 (1H, q, J=8 Hz, C=CH); 6.17 (1H, s, thiazol); 5.65 (1H, dd, J=9 Hz, J=5 Hz, H-7-lactam); 5.60 (1H, d, J=15 Hz, CH$_2$-Py); 5.07 (1H, d, J=5 Hz, H-6-lactam); 5.00 (1H, d, J=15 Hz, CH$_2$-Py); 3.51 (1H, d, J=18 Hz, S-CH$_2$); 3.08 (1H, d, J=18 Hz, S-CH$_2$); 2.42 (6H, s, Py-3,5-CH$_3$); 1.74 (3H, d, J=8 Hz, C=C—CH$_3$).

21. 7-[1-(2-aminothiazol-4-yl)-1(Z)-propenecarboxamido]-3-(3-chloropyridinium)methyl-3-cephem-4-carboxylate Preparation in analogy to example 13 from 7-amino-3-(3-chloropyridinium)methyl-3-cephem-4-carboxylate.

Yield: 210 mg.

$^1$H-NMR (D$_6$-DMSO)

δ=9.92 (1H, s, H-2-Py); 9.50 (1H, d, J=6 Hz, H-6-Py); 9.22 (1H, d, J=9 Hz, NH); 8.88 (1H, d, J=8 Hz, H-4-Py); 8.22 (1H, dd, J=8 Hz, J=6 Hz, H-5-Py); 6.98 (2H, bs, NH); 6.30 (1H, q, J=8 Hz, C=CH); 6.18 (1H, s, thiazol); 5.68 (2H, m, H-7-lactam, CH$_2$-Py); 5.11 (1H, d, J=5 Hz, H-6-lactam); 5.08 (1H, J=15 Hz, CH$_2$-Py); 3.54 (1H, d, J=18 Hz, S-CH$_2$); 3.16 (1H, d, J=18 Hz, S-CH$_2$); 1.76 (1H, d, J=8 Hz, C=C—CH$_3$).

22. 7-[1-(2-aminothiazol-4-yl)-1(Z)-propencarboxamido]-3-(3-aminocarbonylpyridinium)methyl-3-cephem-4-carboxylate The compound was made in analogy to example 13 from 7-amino-3-(3-aminocarbonylpyridinium)methyl-3-cephem-4-carboxylate.

Yield: 540 mg.

$^1$H-NMR (D$_6$-DMSO)

δ=9.78 (2H, m, H-2,6-Py); 9.21 (1H, d, J=9 Hz, NH); 8.94 (1H, d, J=8 Hz, H-4-Py); 8.28 (1H, m, H-5-Py); 6.98 (2H, bs, NH$_2$); 6.29 (1H, q, J=8 Hz, C=CH); 6.18 (1H, s, thiazol); 5.73 (1H, d, J=15 Hz, CH$_2$-Py); 5.69 (1H, dd, J=9 Hz, J=5 Hz, H-7-lactam); 5.20 (1H, d, J=15 Hz, CH$_2$-Py); 5.11 (1H, d, J=5 Hz, H-6-lactam); 3.47 (1H, d, J=18 Hz, S-CH₂); 3.17 (1H, d, J=18 Hz, S-CH₂); 1.75 (3H, d, J=8 Hz, C=C—CH₃).

23. 7-[1-(2-aminothiazol-4-yl)-1(Z)-propencarboxamido]-3-(4-aminocarbonylpyridinium)methyl-3-cephem-4-carboxylate Preparation in analogy to example 13 from 7-amino-3-(4-aminocarbonylpyridinium)methyl-3-cephem-4-carboxylate.

Yield: 350 mg.

¹H-NMR (D₆-DMSO)

δ=9.62 (2H, d, J=6 Hz, H-2,6-Py); 9.17 (1H, d, J=9 Hz, NH); 8.42 (2H, d, J=6 Hz, H-3,5-Py); 6.96 (2H, bs, NH₂); 6.28 (1H, q, J=8 Hz, C=CH); 5.71 (1H, d, J=18 Hz, CH₂-Py); 5.68 (1H, dd, J=5 Hz; H-7-lactam); 5.13 (9 H, d, J=5 Hz, CH₂-Py); 5.09 (1H, d, J=5 Hz, H-6-lactam); 3.55 (1H, d, J=18 Hz, S-Ch₂); 3.08 (1H, d, J=18 Hz, S-CH₂); 1.75 (3H, d, J=8 Hz, C=C—CH₃).

24. 7-[1-(2-aminothiazol-4-yl)-1(Z)-propencarboxamido]-3-pyridiniummethyl-3-cephem-carboxylic acid chloride hydrochloride Under nitrogen atmosphere 7.0 g (38.6 mM) of 1-(2-aminothiazol-4-yl)-1(Z)-propencarboxylic acid were dissolved in 100 ml DMF and 7.4 ml (42.8 mM) of ethyldiisopropylamine were added at 20° C. Whilst stirring it was cooled to −55° C., then 3.1 ml (40 mM) of mesylchloride were added and the mixture was stirred for 40 min. In the meantime 10.7 g (29 mM) of 7-amino-3-pyridiniummethyl-3-cephem-4-carboxylic acid chloride hydrate (containing additional 0.7 Molequiv. HCl) in 12 ml water and 5.8 ml (41 mM) of triethylamine were adjusted to pH 7 and cooled to 10° C. The −55° C. cold DMF-solution was poured into this mixture under stirring while the pH was maintained at 9.5 by adding triethylamine. After 10 min. it was cooled to 0° C. and adjusted to pH 1.5-2 with conc. 12 n HCl. Then additional 50 ml 12 n HCL were added and thereafter 600 ml i-propanol in total were added within 2 hours while the product crystallized. After stirring 1 hour in an ice bath the product was sharply succed off and washed with i-propanol and ether. Yield 10.6 g (64%) product-dihydrate.

NMR-signals (in CD₃OD) at:

δ=9.1 (2H), 8.64 (1H), 8.18 (2H), 6.7 (1H), 6.46 (1H), 5.95 (1H), 5.85 (1H), 5.48 (1H), 5.3 (1H), 3.75 (1H), 3.4 (1H) and 1.98 ppm (3H).

Analysis: Calc.: C 42.4, H 4.4, Cl 12.5, N 12.4, S 11.3. Found: C 42.0, H 4.4, Cl 12.5, N 12.3 S 11.2.

It will be appreciated that the instant specification and examples are set forth by way of illustration and not limitation, and that various modifications and changes may be made without departing from the spirit and scope of the present invention.

What is claimed is:

1. A compound of the formula

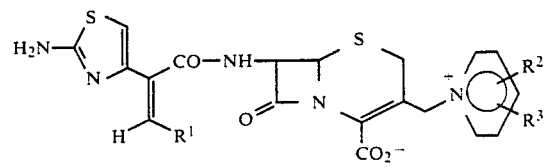

in which

R¹ is C₁-C₆-alkyl, phenyl of halogen-substituted phenyl, and

R² and R³ each independently is H, C₁-C₄-alkyl, chlorine, bromine, carbamoyl or N-C₁-C₄-alkylcarbamoyl.

2. A compound according to claim 1, in which
R¹ is C₁-C₅-alkyl,
R³ is hydrogen, and
R² is H, C₁-C₂-alkyl, carbamoyl, chlorine of bromine.

3. A compound according to claim 1, in which R₂ and R₃ each is H.

4. A compound according to claim 1, in which said compound is 7-[1-(2-aminothiazol-4-yl)-1(Z)-propenecarboxamido]-3-pyridiniummethyl-3-cephem-4-carboxylate of the formula

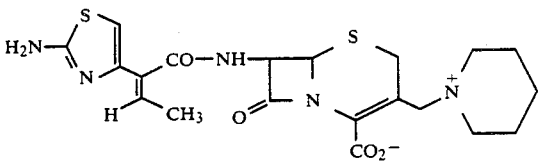

5. A compound according to claim 1, in which said compound is 7-[1-(2-aminothiazol-4-yl)-1(Z)-butenecarboxamido]-3-pyridiniummethyl-3-cephem-4-carboxylate of the formula

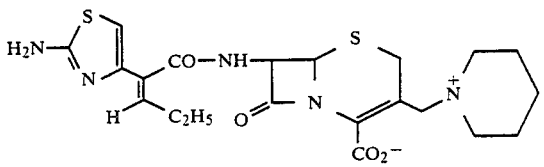

6. A compound according to claim 1, in which said compound is 7-[1-(2-aminothiazol-4-yl)-1(Z)-pentenecarboxamido]-3-pyridiniummethyl-3-cephem-4-carboxylate of the formula

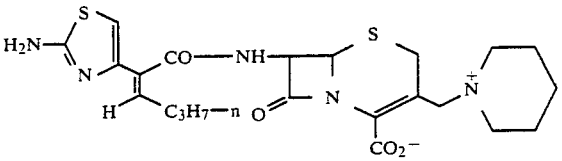

7. A compound according to claim 1, in which said compound is 7-[1-(2-aminothiazol-4-yl)-1(Z)-heptenecarboxamido]-3-pyridiniummethyl-3-cephem-4-carboxylate of the formula

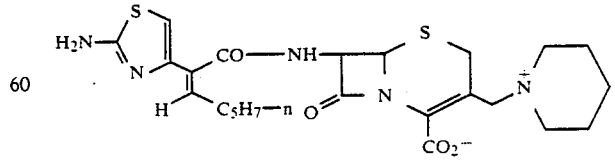

8. A compound according to claim 1, in which said compound is 7-[1-(2-aminothiazol-4-yl)-1(Z)-propenecarboxamido]-3-(4-aminocarbonylpyridiniummethyl)-3-cephem-4-carboxylate of the formula

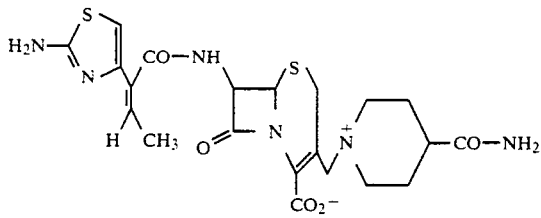

9. An antibacterial composition comprising an antibacterially effective amount of a compound according to claim 1 in admixture with a diluent.

10. A composition according to claim 9 in the form of a tablet, pill, capsule or ampule.

11. A method of combating bacteria which comprises administering to such bacteria or a bacteria host an antibacterially effective amount of a compound according to claim 1.

12. The method according to claim 11, wherein such compound is
7-[1-(2-aminothiazol-4-yl)-1(Z)-propenecarboxamido]-3-pyridiniummethyl-3-cephem-4-carboxylate,
7-[1-(20aminothiazol-4-yl)-1(Z)-butenecarboxamido]-3-pyridiniummethyl-3-cephem-4-carboxylate,
7-[1-(2-aminothiazol-4-yl)-1(Z)-pentenecarboxamido]-3-pyridiniummethyl-3-cephem-4-carboxylate,
7-[1-(2-aminothiazol-4-yl)-1(Z)-heptenecarboxamido]-3-pyridiniummethyl-3-cephem-4-carboxylate, or
7-[1-(2-aminothiazol-4-yl-1(Z)-propenecarboxamido]-3-(4-aminocarbonylpyridiniummethyl)-3-cephem-4-carboxylate.

* * * * *